United States Patent [19]

Hirai et al.

[11] 4,070,401

[45] Jan. 24, 1978

[54] METHOD FOR THE PREPARATION OF A HALOGENATED AROMATIC AMINE

[75] Inventors: Yutaka Hirai; Katsuharu Miyata, both of Omuta, Japan

[73] Assignee: Mitsui Toatsu Chemicals Inc., Tokyo, Japan

[21] Appl. No.: 331,834

[22] Filed: Feb. 12, 1973

[30] Foreign Application Priority Data

Feb. 19, 1972  Japan ................................. 47-17546
Feb. 28, 1972  Japan ................................. 47-19724

[51] Int. Cl.$^2$ ............................................. C07C 85/11
[52] U.S. Cl. ............................ 260/580; 260/518 A; 260/575
[58] Field of Search ........................................ 260/580

[56] References Cited

U.S. PATENT DOCUMENTS

| 3,361,819 | 1/1968 | Kosak et al. | 260/580 |
| 3,499,034 | 3/1970 | Gonzalez | 260/580 |
| 3,546,297 | 12/1970 | Kosak | 260/580 |

Primary Examiner—Joseph Paul Brust

[57] ABSTRACT

A method for the preparation of a halogenated aromatic amine, wherein a halogenated aromatic nitro compound is hydrogenated in liquid phase in the presence of a platinum-base catalyst to obtain a corresponding halogenated aromatic amine, the hydrogenation being carried out in the presence of an alkylmonoamine, an alicyclic amine or a polyalkylenepolyamine. The presence of the amine well suppresses a dehalogenation reaction which would otherwise be involved, so that not only a high purity halogenated aromatic amine is obtained, but also corrosion of a reactor is prevented.

10 Claims, No Drawings

METHOD FOR THE PREPARATION OF A HALOGENATED AROMATIC AMINE

BACKGROUND OF THE INVENTION

This invention relates to a method for the preparation of a halogenated aromatic amine, wherein a halogenated aromatic nitro compound is hydrogenated in liquid phase to give a corresponding halogenated aromatic amine.

Generally, it is well known in the art that when a halogenated aromatic nitro compound is hydrogenated, there occurs dehalogenation reaction as well as reduction of the nitro groups, so that qualities and yield of the resultant halogenated aromatic amine become lower. Furthermore, hydrogen chloride which is produced by the dehalogenation reaction greatly contributes to corrosion of the reactor. Accordingly, it is required that the dehalogenation reaction be suppressed to a minimum in the hydrogenation of the halogenated aromatic nitro compound. There have been heretofore known various methods for suppressing the dehalogenation reaction, including a method of using a metallic sulfide as a catalyst and a method of adding a dehalogenation inhibitor. In this connection, there are described methods of using sulfides of noble metals as a catalyst in French Pat. No. 1,417,236 and also by Harold Greenfield et al (Journal of Organic Chemistry, Vol. 32 Page 3670). However, the sulfide catalysts are disadvantageously lower in catalytic activity than noble metal catalysts, and higher in production cost since they require complicated preparation process.

Furthermore, there are known a variety of methods of conducting hydrogenation by the addition of a dehalogenation inhibitor, for example, a method of using a platinum-base catalyst together with magnesium oxide or hydroxide as a dehalogenation inhibitor (British Pat. Specification No. 859,251), a method of using a morpholine or a piperizine (U.S. Pat. No. 3,145,231), a method of using divalent nickel and trivalent chromium ions together with ammonia, a morpholine or a piperazine (U.S. Pat. No. 3,546,297), a method of using triphenylphosphite or tritollylphosphite (U.S. Pat. No. 3,474,144), etc.

Among these, the method of U.S. Pat. No. 3,546,297 has a disadvantage that though little dehalogenation reaction occurs, the preparation of the catalyst including nickel and chromium is very complicated, the loss of the ammonia during operation is large in amount due to its high volatility particularly where ammonia is used, so that it is difficult to handle ammonia quantitatively. Furthermore, any of methods of British Pat. Specification No. 859,251 and U.S. Pat. Nos. 3.145.231 and 3,474,144 is disadvantageous in that the effect of inhibiting dehalogenation is insufficient.

As for a method of using a catalyst other than of platinum, there is known a method of employing nickel as a catalyst and as an inhibitor an inorganic alkali or salt thereof such as magnesium hydroxide (U.S. Pat. Nos. 3,051,753 and 3,067,253) or a method of using a thiocyanate as an inhibitor (British Pat. Specification No. 1,191,610). However, the abovementioned methods are inferior in effects in inhibiting dehalogenation to the method employing a platinum catalyst.

SUMMARY OF THE INVENTION

The inventors have conducted an extensive study on suppression or inhibition of halogenation reaction which would occur during preparation of a halogenated aromatic amine. As a result, the inventors discovered that when a halogenated aromatic nitro compound is hydrogenated in the presence of a predetermined amount of a platinum catalyst together with an amine selected from the group consisting of an alkylmonoamine, an alicyclic amine and a polyalkylenepolyamine, the dehalogenation may be suppressed to a minimum. The present invention has been completed on the basis of this discovery. The alkylmonoamine, alicyclic amine and polyalkylenepolyamine have common properties that they are an organic nitrogen-containing base having a dissociation constant $pK_b$ lower than 4.2. The dissociation constant herein described means that which is defined according to the dissociation equilibrium of the usual acid or base, i.e., when an organic nitrogen-containing base is expressed by RN, the dissociation equilibrium of RN is expressed by a formula $$RN + H_2O \rightleftarrows RNH^+ + OH^-$$

and the dissociation constant is defined as follows

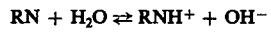

$$pK_b = - \log \frac{[RNH^+][OH^-]}{[RN]}$$

where [ ] means activity.

Though the dissociation constant $pK_b$ is generally more or less varied with temperature, the $pK_b$ value is measured at 25° C herein.

A primary object of the invention is to provide a method of preparing a halogenated aromatic amine while suppressing a dehalogenation reaction to a minimum degree.

A feature accompanied with the above object is that not only the yield of the halogenated aromatic amine obtained by the reaction is increased and the resultant amine has high purity, but also the corrosion of a reactor can also be suitably prevented.

The continued study by the inventors has also been led to a discovery that the suppression of dehalogenation reaction can further be improved by hydrogenating the halogenated aromatic nitro compound in the coexistence of an amine selected from the group consisting of an alkylmonoamine and an alicyclic amine and of a polyalkylenepolyamine, together with a predetermined amount of a platinum catalyst. The alkylmonoamine, alicyclic amine and polyalkylenepolyamine are an organic nitrogen-containing base having a disassociation constant $pK_b$ lower than 4.2, as described hereinbefore. To a surprise, where the alkylmonoamine or alicyclic amine is used together with the polyalkylenepolyamine as a dehalogenation inhibitor, the dehalogenation suppression effects become remarkably greater.

DETAILED DESCRIPTION OF THE INVENTION

The alkylmonoamines used in the present invention are, for example, methylamine, dimethylamine, trimethylamine, ethylamine, diethylamine, triethylamine, propylamine, dipropylamine, isopropylamine, disopropylamine, n-butylamine, di-n-butylamine, isobutylamine, hexylamine, dihexylamine, heptylamine, octylamine, dioctylamine, nonylamine, n-amylamine, isoamylamine, decylamine, dodecylamine, didocecylamine, undecylamine, tridecylamine, ditridecylamine, tetradecylamine, pentadecylamine, dipentadecylamine, hexadecylamine, octadecylamine and dioctadecylamine.

The alicyclic amines of the present invention include cyclohexylamine, dicyclohexylamine, 1,2-, 1,3-, 1,4-diaminocyclohexane, and isopropyridenebis(4-aminocyclohexane).

Furthermore, the polyalkylenepolyamine used in the present invention are as follows: diethylenetriamine, triethylenetetramine, tetraethylenepentamine, pentaethylenehexamine, dipropylenetriamine, tripropylenetetramine, tetrapropylenepentamine, pentapropylenehexamine, dibutylenetriamine, dipentylenetriamine, dihexylenetriamine, N,N,N',N'',N''-pentamethyldiethylenetriamine, 6,6',6''-tris(dimethylamino) trihexylamine, 6,6',6''-tris(diethylamino) trihexylamine, 6,6',6''-tris(dipropylamino) trihexylamine, and 2,2', 2'-triaminotriethylamine.

Though the amount to be used of the alkylamine, alicyclic amine, or polyalkylenepolyamine (hereinafter referred to simply as amine) is varied with the kind of the halogenated nitro compound which is used as a starting material, the amine is generally used in an amount more than 1 part by weight per 1000 parts of the halogenated nitro compound. If the amount of the amine is too small, the effects of the dehalogenation is reduced to a considerable degree. Furthermore, though it is possible to employ the amine in an amount equal to or more than that of the halogenated nitro compound, it is meaningless in most cases to use such a large amount of the amine. The polyalkylenepolyamine gives remarkable dehalogenation inhibition effects when employed in a large amount, but the reaction velocity becomes slower. In this connection, if a small amount of the polyalkylenepolyamine is used, the dehalogenation inhibition effects become insufficient. On the other hand, where the alkylmonoamine or alicyclic amine is used alone, it gives greater effects of dehalogenation inhibition as compared with the conventional methods mentioned hereinbefore, but in many cases, the degree of the effects is not insufficient. However, even an extremely small amount of the polyalkylenepolyamine exhibits remarkable dehalogenation inhibition effects when used together with the alkylmonoamine or alicyclic amine. The dehalogenation reaction is therefore suppressed to a degree far less than in the cases using the respective amines alone, and the hydrogenation reaction velocity becomes higher.

The amount to be used of the polyalkylenepolyamine is varied with the kind of the halogenated nitro compound which is used as a starting material, but generally a good result is obtained by the introduction of a small amount of the polyalkylenepolyamine, viz., 1 part by weight per 10 – 10000 parts of a halogenated nitro compound used as a starting material. On the other hand, it is necessary to use an alkylmonoamine or alicyclic amine in an amount slightly greater than the polyalkylenepolyamine, preferably 1 part by weight per 1 – 1000 parts of a halogenated nitro compound used.

A platinum catalyst used in the present invention may be a conventional or known dehydrogenation catalyst, and may be employed without use of a carrier. However, it would be better to use a carrier in practical applications. A known carrier material such as of active carbon, carbon black, alumina, diatomaceous earth or the like may be employed in the present invention. The concentration of platinum with respect to the carrier is preferred to be within a range of 1 part by weight per 1000 – 10 parts of the carrier. If the platinum is used in an excessive amount with respect to a halogenated nitro compound, dehalogenation tends to occur in an increased amount. On the contrary, if the amount of platinum is too small, the reaction velocity becomes disadvantageously slow in practical applications. Platinum is preferred to be 1 part by weight per 10,000 – 1,000,000 parts of a halogenated nitro compound. Platinum may be used in combination with other metals such as palladium, rhenium, ruthenium and rhodium, and a promoter such as of iron, cobalt, nickel, chromium, or the like may be further added to the combination.

The halogenated aromatic amine of the present invention can readily be prepared by a conventional pressurized hydrogenation method using an autoclave, but may be prepared by a reaction under normal pressure. The reaction conditions are varied with the kind of the halogenated nitro compound which is used as a starting material, but generally the reaction may be conducted at a reaction temperature of 30° to 200° C under a pressure of 0 to 200 kg/cm$^2$G. A solvent may be used, if necessary.

Any existing halogenated aromatic nitro compound can be converted into the corresponding halogenated aromatic amine by the method of the present invention. Examples of producible halogenated aromatic amine are, for example, halogenated anilines such as o-, m-, p-chloroaniline, m-bromoaniline p-fluoroaniline, and 2,3-, 2,4-, 2,5-, 3,4-dichloroaniline; halogenated aminophenols such as 3-bromo-, 3-chloro or 3-fluoro-4-aminophenol, 2,3-dichloro-4-aminophenol, etc.; halogenated aminodiphenyls such as 4-fluoro, 4-chloro or 4-bromo-3-aminodiphenyl, etc.; alkylhalogenated aniline such as 4-chloro-2-aminotoluene, etc.; and halogenated aminophenylcarboxylic acids such as 6-chloro-2-aminobenzoic acid, etc.

Where a halogenated aromatic nitro compound is hydrogenated by the method of the present invention, the dehalogenation reaction occurs in a degree far less than in a method without use of a dehalogenation inhibitor or in a method using a known dehalogenation inhibitor. As a result, the halogenated aromatic amine obtained has high purity. Furthermore, the suppression of dehalogenation reaction also serves to prevent corrosion of the reactor used.

The platinum catalyst used in the present invention is widely used as a catalyst for hydrogenation and is easily available or can be readily prepared. Additionally, most of amines which are employed as a dehalogenation inhibitor are produced on an industrial scale and at a low cost. Furthermore, an amine is used only in a small amount in the present invention. This is, needless to say, greatly advantageous from an industrial point of view.

The invention will be particularly illustrated in the following Examples. The reaction products are analyzed by a gaschromatography after a catalyst used is filtered, and composition shown in Examples do not include a solvent, additives used and water produced.

EXAMPLE 1

100 g of 3,4-dichloronitrobenzene, 1 g of triethylenetetramine and 0.02g of 5% platinum on carbon were introduced into a SUS-32 eletromagnetic agitation type autoclave having an inner volume of 500 ml. After air in the autoclave was replaced by hydrogen, a hydrogen gas was further charged therein under a pressure of 20 kg/cm$^2$G. The mixture was heated up to 100° C with agitation. Then, a hydrogen gas was further introduced into the autoclave until the pressure reached 50 kg/cm$^2$G, and the mixture was reacted at 100° C. During the reaction, whenever the reaction pressure drops down to 30 kg/cm²G, fresh hydrogen gas was charged into the autoclave until the pressure of 50 kg/cm² was restored. The hydrogen charging was repeated until absorption of hydrogen was no longer recognized. The reaction took about 150 minutes. After the absorption of hydrogen became unrecognizable, the reaction system was kept warm for 1 hour with agitation, at a temperature slightly higher than the reaction temperature, so as to complete the reaction. Then, the autoclave was cooled and the reaction product was discharged therefrom. To the reaction product was added the same amount of methanol to give a uniform solution. Thereafter, the catalyst was filtered out and the resultant product was analyzed by gaschromatography. The analysis revealed that the reaction product contained therein a trace (less than 0.01% by weight) of aniline which was produced by a dehalogenation reaction, 0.4% by weight of monochloroaniline and 98.5% by weight of 3,4-dichloroaniline. The pH value of the resultant reaction liquid was within a range of 7 to 8 and no corrosion occurred to the reactor.

When tetraethylenepentamine or pentaethylenehexamine was used instead of triethylenetetramine in the above reaction, similar results were obtained.

Furthermore, when 2,5-dichloronitrobenzene was used instead of 3,4-dichloronitrobenzene for hydrogenation, a high yield of dichloroaniline was obtained as in Example 1.

EXAMPLE 2

3,4-dichloronitrobenzene was hydrogenated in the same manner as in Example 1 except that 1.0 g of isopropylamine was used instead of triethylenetetramine. The reaction took about 90 minutes. The resultant reaction product contained therein a trace of aniline, 0.4% by weight of monochloroaniline, and 98.8% by weight of 3,4-dichloroaniline. The pH value of the resultant reaction liquid was within a range of 9 to 10 and no corrosion of the reactor was observed.

Furthermore, when monomethylamine, dimethylamine, trimethylamine, ethylamine, diethylamine, triethylamine, n-propylamine, n-butylamine, secbutylamine and hexylamine were used instead of isopropylamine, similar results were also obtained.

EXAMPLE 3

Example 1 was repeated except that 2.0g of cyclohexylamine were used instead of triethylenetetramine for the hydrogenation of 3,4-dichloronitrobenzene. After the reaction period of about 60 minutes, the resultant reaction product contained a trace of aniline, 0.4% by weight of monochloroaniline, and 98.8% by weight of 3,4-dichloroaniline. The pH value of the resultant reaction liquid was within a range of 9 to 10 and no corrosion was observed on the reactor walls.

COMPARATIVE EXAMPLE 1

Example 1 was repeated except that triethylenetetramine was not employed for the hydrogenation of 3,4-dichloronitrobenzene. The resultant reaction product contained 0.2% by weight of aniline, 1.4% by weight of monochloroaniline, 88.7% by weight of 3,4-dichloroaniline and 9.7% by weight of the unknown having a melting point higher than 3,4-dichloroaniline. The pH value of the resultant reaction liquid was 1, and the inner walls of the autoclave and the agitator were considerably corroded.

COMPARATIVE EXAMPLE 2

Example 1 was repeated except that 2.0 g of morpholine was used instead of triethylenetetramine for the hydrogenation of 3,4-dichloronitrobenzene. The resultant reaction product contained 0.2% by weight of aniline, 1.0% by weight of monochloroaniline, 94.6% by weight of 3,4-dichloroaniline and 4.2% by weight of the unknown. The pH value of the resultant reaction liquid was within a range of 3 to 4. Thus, the inhibition effects on dehalogenation were insufficient as compared with those in Examples 1 to 3, and the inner walls of the autoclave and agitator were corroded.

EXAMPLE 4

100 g of p-chloronitrobenzene, 200 g of methanol, 0.02 g of 5% platinum on carbon, and 1.0 g of tetraethylenepentamine were used and treated in the same manner as in Example 1 for conducting a hydrogenation reaction. The reaction took about 210 minutes. The pH value of the resultant reaction liquid was 8, and the reaction product contained 0.1% by weight of aniline and 98.9% by weight of p-chloroaniline.

Where o-chloronitrobenzene was used instead of p-chloronitrobenzene, the reaction occurred in the same manner to give a high yield of o-chloroaniline.

EXAMPLE 5

100 g of o-chloronitrobenzene, 0.04 g of 5% platinum on carbon, and 2.0 g of octadecylamine were treated in the same manner as in Example 1 for conducting the hydrogenation reaction. The reaction took about 120 minutes. The pH value of the resultant reaction liquid was within a range of 8 to 9, and the reaction product contained 0.5% by weight of aniline and 98.9% by weight of o-chloroaniline.

Where decylamine, pentadecylamine or dioctadecylamine was used instead of octadecylamine, similar results were obtained.

EXAMPLE 6

100 g of p-chloronitrobenzene, 200 g of methanol, 0.1 g of tetraethylenepentamine, 4.0 g of cyclohexylamine and 0.02 g of 5% platinum on carbon were treated in the same manner as in Example 1 for conducting the hydrogenation reaction. The reaction took about 100 minutes.

The reaction product contained a trace (less than 0.01% by weight) of aniline and 99.9% by weight of p-chloroaniline. The pH value of the resultant reaction liquid was about 9.

EXAMPLES 7 - 8

Example 6 was repeated except that 4.0 g of methylamine or 4.0 g of isopropylamine were used instead of cyclohexylamine for the hydrogenation of p-chloronitrobenzene and reaction conditions shown in Table 1 were used. The analytical or test results were shown in Table 1 below.

From the results shown, it will be seen that a production amount of aniline is very small and great dehalogenation inhibition effects are noted both in Examples 7 and 8. The resultant reaction liquids were alkaline and no corrosion occurred to the reactor.

On the other hand, where a dehalogenating agent is not used, there occurred a dehalogenation reaction to an extreme degree, and a yield of p-chloroaniline was lower than 50%. The pH value of the resultant reaction liquid was within a range of 1 to 2 and corrosion occurred considerably and this method is unsuitable for the preparation of a halogenated aniline.

While, where 0.1 g of tetraethylenepentamine alone was used as a dehalogenating agent, or where 4.0 g of cyclohexylamine as the agent, 0.5 to 1% by weight of aniline was secondarily produced in both cases. Thus, the use of the tetraethylenepentamine or cyclohexylamine alone gave rather remarkable effects for inhibition of dehalogenation as compared with a case where no dehalogenation agent is used, but only in a degree inferior to those obtained from combination of two compounds as in Example 6.

Table 1

| Example No. | Additive Compound | Dissociation Constant pK$_b$ | Reaction Temperature (° C) | Reaction Time (min) | pH of Resultant Reaction Liquid | Composition of Reaction Product (%) | | |
|---|---|---|---|---|---|---|---|---|
| | | | | | | Aniline | p-chloro-aniline | Others |
| 7 | methylamine | 3.4 | 100 | 70 | 9 | 0.2 | 99.3 | 0.5 |
| 8 | isopropylamine | 3.4 | 90 | 80 | 9 - 10 | 0.1 | 99.6 | 0.2 |

EXAMPLES 9 – 12

Example 6 was repeated except that diethylenetriamine, triethylenetetramine, N,N,N',N'',N''-pentamethyldiethylenetriamine and pentaethylenehexamine were used instead of tetraethylenepentamine, respectively, for hydrogenation of p-chloronitrobenzene, and reaction conditions shown in Table 2 were employed in the respective Examples. As shown in Table 2, there was secondarily produced only a small amount of aniline and distinct dehalogenation inhibition effects were recognized in all Examples.

EXAMPLES 13 – 15

Example 6 was repeated except that o-chloronitrobenzene, 3,4-dichloronitrobenzene, and 2,5-dichloronitrobenzene were used instead of p-chloronitrobenzene, respectively, for conducting a hydrogenation reaction, and reaction conditions shown in Table 3 were employed. As a result, aniline or chloroaniline which was secondarily produced by dehalogenation reaction was only in a small amount, thus showing excellent effects of dehalogenating inhibition in all Examples as shown in Table 3.

anilines and halogenated aminophenylcarboxylic acids by catalytic, liquid-phase hydrogenation in the presence of a platinum catalyst, the improvement consisting of hydrogenating said nitro compound in the presence of:

a. 1 part by weight of platinum per 10,000–1,000,000 parts of said nitro compound, and b. 1 part by weight of an amine dehalogenation inhibitor selected from the group consisting of (i) an alkylmonoamine selected from methylamine, dimethylamine, trimethylamine, ethylamine, diethylamine, triethylamine, propylamine, dipropylamine, isopropylamine, di-isopropylamine, n-butylamine, di-n-butylamine, isobutylamine, hexylamine, dihexylamine, heptylamine, octylamine, dioctylamine, nonylamine, n-amylamine, isoamylamine, decylamine, dodecylamine, didocecylamine, undecylamine, tridecylamine, ditridecylamine, tetradecylamine, pentadecylamine, dipentadecylamine, hexadecylamine, octadecylamine, and dioctadecylamine, (ii) an alicyclic amine selected from cyclohexylamine, dicyclohexlamine, 1,2-, 1,3-, 1,4-diaminocyclohexane and isopropyridenebis-(4-aminocyclohexane) and (iii) a polyalkylenepolyamine selected from diethylenetriamine, triethylenetetramine, tetraethylenepentamine, pentaethylenehexamine, dipropylenetriamine, tripropylenetetramine, tetrapropylenepentamine, pentapropylenehexamine, dibutylenetriamine, dipentylenetriamine, dihexylenetriamine, N, N, N', N'', N'' - pentamethyldiethylenetriamine, 6, 6', 6'' -tris (dimethylamino) trihexylamine, 6, 6', 6'' -tris (diethylamino) trihexylamine, 6, 6', 6'' -tris (dipropylamino) trihexylamine, and 2, 2', 2' -triaminotriethylamine, per 1–1000 parts of said nitro compound, said amine inhibitor having a dissociation constant's value pK$_b$ lower than 4.2.

Table 2

| Example No. | Additive | Reaction Temperature (20° C) | Reaction Time (min) | pH of Resultant Reaction Liquid | Composition of Reaction Product (%) | | |
|---|---|---|---|---|---|---|---|
| | | | | | Aniline | p-chloro-aniline | Others |
| 9 | Diethylenetriamine | 100 | 100 | 9 | 0.2 | 99.2 | 0.6 |
| 10 | Triethylenetetramine | 100 | 100 | 9 | 0.2 | 99.2 | 0.6 |
| 11 | N,N,N',N'',N''-pentamethyl-diethylenetriamine | 100 | 70 | 9 | 0.3 | 99.4 | 0.3 |
| 12 | Pentaethylenehexamine | 100 | 90 | 9 | 0.2 | 99.0 | 0.8 |

Table 3

| Example No. | Starting Material | Reaction Temperature (° C) | Reaction Time (min) | pH of Resultant Reaction Liquid | Composition of Reaction Product (%) | | | |
|---|---|---|---|---|---|---|---|---|
| | | | | | Aniline | Monochloro-aniline | Dichloro-aniline | Others |
| 13 | o-chloronitrobenzene | 100 | 190 | 9 - 10 | Trace | 99.5 | — | 0.5 |
| 14 | 3,4-dichloronitrobenzene | 100 | 40 | 9 | Trace | 0.1 | 99.2 | 0.7 |
| 15 | 2,5-dichloronitrobenzene | 100 | 60 | 9 - 10 | Trace | 0.1 | 99.5 | 0.4 |

What is claimed is:

1. In a method for the conversion of a halogenated aromatic nitro compound to produce the corresponding halogenated aromatic amine selected from the group consisting of halogenated anilines, halogenated aminophenols, halogenated aminodiphenyls, alkylhalogenated 2. The improvement according to claim 1, wherein said amine dehalogenation inhibitor consists of 1 part selected from said (i) and (ii) per 1–1000 parts of said nitro compound and 1 part of said (iii) per 10–10,000 parts of said nitro compound, said amine inhibitor having a dissociation constant's value $pK_b$ lower than 4.2.

3. A method according to claim 1, wherein said halogenated aromatic nitro compound is selected from the group consisting of orthochloronitrobenzene, parachloronitrobenzene, 2,5-dichloronitrobenzene and 3,4-dichloronitrobenzene.

4. A method according to claim 1, wherein the hydrogenation reaction is carried out in methanol.

5. A method according to claim 2, wherein said halogenated aromatic nitro compound is selected from the group consisting of orthochloronitrobenzene, parachloronitrobenzene, 2,5-dichloronitrobenzene and 3,4dichloronitrobenzene.

6. A method according to claim 2, wherein the hydrogenation reaction is carried out in methanol.

7. A method according to claim 2, wherein said amine dehalogenation inhibitor is cyclohexylamine and said polyalkylenepolyamine is tetraethylenepentamine.

8. A method according to claim 1, wherein said alicyclic amine is cyclohexylamine.

9. A method according to claim 1, wherein said polyalkylenepolyamine is triethylenetetramine.

10. A method according to claim 1, wherein said polyalkylenepolyamine is tetraethylenepentamine.

* * * * *